United States Patent [19]

Reiffenrath et al.

[11] Patent Number: 5,211,878
[45] Date of Patent: * May 18, 1993

[54] DIFLUOROBENZONITRILE DERIVATIVES

[75] Inventors: Volker Reiffenrath, Rossdorf; Joachim Krause, Dieburg; Andreas Wächtler, Griesheim; Georg Weber, Erzhausen; Ulrich Finkenzeller, Plankstadt, all of Fed. Rep. of Germany

[73] Assignee: Merck Patent Gesellschaft mit Beschrankter Haftung, Darmstadt, Fed. Rep. of Germany

[*] Notice: The portion of the term of this patent subsequent to Mar. 30, 2010 has been disclaimed.

[21] Appl. No.: 700,955

[22] Filed: May 14, 1991

Related U.S. Application Data

[63] Continuation of Ser. No. 321,427, Mar. 9, 1989, abandoned.

[30] Foreign Application Priority Data

Mar. 10, 1988 [DE] Fed. Rep. of Germany ....... 3807806

[51] Int. Cl.[5] ...................... C09K 19/30; C09K 19/12; G02F 1/13
[52] U.S. Cl. ..................... 252/299.63; 252/299.66; 359/103
[58] Field of Search ........... 252/299.63, 299.6, 299.66; 350/350 R; 558/423, 425

[56] References Cited

U.S. PATENT DOCUMENTS

| 4,368,135 | 1/1983 | Osman | 252/299.63 |
|---|---|---|---|
| 4,415,470 | 11/1983 | Eidenschink et al. | 252/299.63 |
| 4,419,264 | 12/1983 | Eidenschink et al. | 252/299.63 |
| 4,479,885 | 10/1984 | Mukoh et al. | 252/299.63 |
| 4,514,317 | 4/1985 | Tuong et al. | 252/299.63 |
| 4,536,321 | 8/1985 | Sugimori et al. | 252/299.63 |
| 4,545,922 | 10/1985 | Eidenschink et al. | 252/299.63 |
| 4,551,264 | 11/1985 | Eidenschink et al. | 252/299.63 |
| 4,602,851 | 7/1986 | Jenner et al. | 252/299.63 |
| 4,606,845 | 8/1986 | Romer et al. | 252/299.63 |
| 4,637,897 | 1/1987 | Kelly | 252/299.63 |
| 4,659,499 | 4/1987 | Ferrato | 558/414 |
| 4,659,502 | 4/1987 | Fearon et al. | 252/299.63 |
| 4,664,840 | 5/1987 | Osman | 252/299.63 |
| 4,689,176 | 8/1987 | Inoue et al. | 252/299.65 |
| 4,710,315 | 12/1987 | Schad et al. | 252/299.63 |
| 4,724,097 | 2/1988 | Romer et al. | 252/299.63 |
| 4,776,973 | 10/1988 | Bofinger et al. | 252/299.61 |
| 4,797,228 | 11/1989 | Goto et al. | 252/299.63 |
| 4,820,839 | 4/1989 | Krause et al. | 544/316 |
| 4,834,904 | 5/1989 | Krause et al. | 252/299.01 |
| 4,853,152 | 8/1989 | Goto et al. | 252/299.63 |
| 4,855,076 | 8/1989 | Goto et al. | 252/299.63 |
| 4,886,621 | 12/1989 | Sage et al. | 252/299.61 |
| 4,897,216 | 1/1990 | Reiffenrath et al. | 252/299.63 |
| 4,908,152 | 3/1990 | Goto et al. | 252/299.63 |
| 4,910,350 | 3/1990 | Tanaka et al. | 570/129 |
| 4,917,819 | 4/1990 | Goto et al. | 252/299.63 |
| 4,925,278 | 5/1990 | Buchecker et al. | 252/299.63 X |
| 4,925,590 | 5/1990 | Reiffenrath et al. | 252/299.61 |
| 5,087,764 | 2/1992 | Reiffenrath et al. | 568/656 |

FOREIGN PATENT DOCUMENTS

| 0051738 | 3/1981 | European Pat. Off. . |
|---|---|---|
| 0133489 | 7/1984 | European Pat. Off. . |
| WO88/02130 | 3/1988 | World Int. Prop. O. . |

OTHER PUBLICATIONS

Finkenzeller et al., "Physical Properties of Liquid Crystals: III. Dielectric Permittivities," Liquid Crystal Newsletter, Mar. 4, 1989, Merck Group.

*Primary Examiner*—Robert L. Stoll
*Assistant Examiner*—C. Harris
*Attorney, Agent, or Firm*—Millen, White, Zelano & Branigan

[57] ABSTRACT

Derivatives of 2,3-difluorobenzonitrile of the formula I

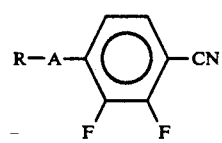

are useful components of liquid crystalline phases.

21 Claims, No Drawings

DIFLUOROBENZONITRILE DERIVATIVES

This application is a continuation of application Ser. No. 07/321,427, filed Mar. 9, 1989, now abandoned.

CROSS-REFERENCE TO RELATED APPLICATIONS

This application is related to commonly assigned applications of even date, Ser. Nos. 321,045; 321,426; and 321,428 each of which is entirely incorporated by reference herein.

SUMMARY OF THE INVENTION

The invention relates to derivatives of 2,3-difluorobenzonitrile of the formula I

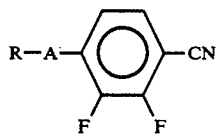

in which
R is an alkyl group having 1-12 C atoms, in which one or two CH$_2$ groups may also replaced by —O—, —CO—, —O—CO— and/or —CH=CH—, where two O atoms are not directly linked with one another, and
A is

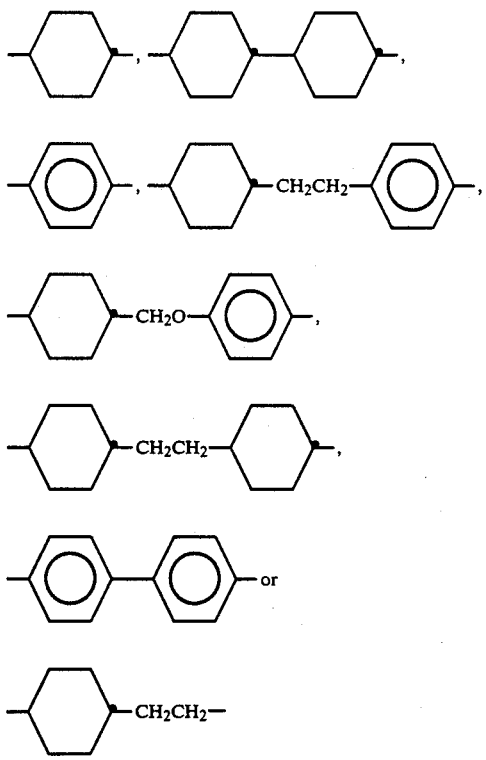

For the sake of simplicity, in the following Cyc is a 1,4-cyclohexylene group, PF2N is a group of the formula

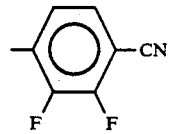

and Phe is a 1,4-phenylene group.

The compounds of the formula I can be used as components of liquid crystalline phases, in particular for displays which are based on the principle of the twisted cell, the guest-host effect, the effect of deformation of aligned phases or the effect of dynamic scattering.

An important criterion for the multiplex operation of such cells is a small ratio of the anisotropy of the dielectric constant to the dielectric constant perpendicular to the molecular axis, i.e. of $\Delta\epsilon/\epsilon_\perp$ (compare, for example, Gharadjedagji, F. et al., Rev. Phas. Appl. 11, 1976 (467)).

In order to achieve a small $\Delta\epsilon/\epsilon_\perp$, conventional substances having a negative $\Delta\epsilon$ are mixed with substances having a positive $\Delta\epsilon$.

However, it is better to employ substances which have a strong transverse dipole in addition to a positive $\Delta\epsilon$. A series of liquid crystalline compounds of this type have already been synthesized, thus, for example, carboxylic acid esters of 4-cyano-2(3)-fluorophenol or 5-cyanopyridin-2-yl compounds.

However, the latter in general have disadvantages, such as, for example, poor solubility in mixtures, high viscosity, high melting points and chemical instability. In addition, as a rule, they have a strong tendency to form smectic phases of higher order. A need therefore exists for further compounds having positive dielectric anisotropy combined with a large dielectric constant perpendicular to the molecular axis which permits the properties of mixtures for all types of electrooptical applications to be improved further.

The invention involves the finding of stable liquid crystalline or mesogenic compounds having a positive dielectric anisotropy, a large regative transverse dipole and, at the same time, a low viscosity.

It has been found that the compounds of the formula I are excellently suited as components of liquid crystalline phases. In particular, stable liquid crystalline phases having a wide mesophase region and comparatively low viscosity can be prepared with their aid.

With the preparation of the compounds of the formula I, the range of liquid crystalline substances which are suitable under various industrial application standpoints for the preparation of liquid crystalline mixtures is in addition very generally considerably widened.

The compounds of the formula I have a wide range of application. Depending on the choice cf substituents, these compounds can be used as base materials of which liquid crystalline phases are, for the prodominant part, composed; however, liquid crystalline base materials from other classes of compounds can also be added to compounds of the formula I, in order, for example, to vary the dielectric and/or optical anisotropy and/or the viscosity and/or the spontaneous polarization and/or the phase ranges and/or the tilt angle and/or the pitch of such a dielectric.

The compounds of the formula I are in addition suitable as intermediates for the preparation of other substances which can be used as constituents of liquid crystalline dielectrics.

The compounds of the formula I are colorless in the pure state and form liquid crystallines mesophases in a temperature range which is placed favorably for electrooptical use. They are very stable chemically, thermally and towards light.

The invention therefore relates to the compounds of the formula I.

Furthermore, the invention relates to the use of the compounds of the formula I as components of liquid crystalline phases. The invention in addition relates to liquid crystalline phases containing at least one compound which contains a 2,3-difluoro-4-cyanophenyl radical as a structure element, in particular a compound of the formula I, and also liquid crystal display elements which contain phases of this type. Phases of this type have particularly advantageous elastic constants and are particularly suitable on account of their low $\Delta\epsilon/\epsilon_\perp$ values for TFT mixtures.

The compounds of the formula I accordingly include compounds having two rings of the sub-formulae Ia to Ic:

R—Phe—PF2N  Ia

R—Cyc—PF2N  Ib

R—Cyc—CH2CH2—PF2N  Ic and compounds having three rings of the sub-formulae Id to Ih:

R—Phe—Phe—PF2N  Id

R—Cyc—Cyc—PF2N  Ie

R—Cyc—CH2CH2—Cyc—PF2N  If

R—Cyc—CH2O—Phe—PF2N  Ig

R—Cyc—CH2CH2—Phe—PF2N  Ih

In the compounds of the formulae above and below, R is preferably alkyl, and in addition alkoxy.

R in the formulae above and below preferably has 2–10 C atoms, in particular 3–7 C atoms. One or two CH2 groups in R can also be replaced. Preferably, only one CH2 group is replaced by —O—, —CO— or —CH=CH—, in particular by —O— or —O—CO—.

In the formulae above and below, R is preferably alkyl, alkoxy or another oxaalkyl group, and in addition also alkyl groups in which one or more CH2 groups can be replaced by a grouping selected from the group comprising —O—, —O—CO—, —CH=CH— or else by a combination of two suitable groupings, in which two heteroatoms are not directly linked with one another.

If R is an alkyl radical in which one ("alkoxy" or "oxaalkyl") or two ("alkoxyalkoxy" or "dioxaalkyl") non-adjacent CH2 groups can also be replaced by O atoms, then this can be linear or branched. Preferably, it is linear, has 2, 3, 4, 5, 6 or 7 C atoms and is therefore preferably ethyl, propyl, butyl, pentyl, hexyl, heptyl, ethoxy, propoxy, butoxy, pentoxy, hexoxy or heptoxy, and in addition methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably linear 2-oxypropyl (=methoxymethyl), 2- (=ethoxymethyl) or 3-oxabutyl (=2-methoxyethyl), 2-, 3- or 4-oxapentyl, 2-, 3-, 4- or 5- oxahexyl, 2-, 3-, 4-, 5- or 6-oxaheptyl. 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4-, 1,5-, 2,4-, 2,5-, or 3,5-dioxadexyl, pentyl, 1,3-, 1,4-, 1,5-, 2,4-, 2,5- or 3,5-dioxahexyl, or 1,3-, 1,4-, 1,5-, 1,6-, 2,4-, 2,5-, 2,6-, 3,5-, 3,6- or 4,6-dioxaheptyl.

If R is an alkyl radical in which one CH2 group -CH=CH-, it can be linear or branched. Preferably, it is linear and has 2 to 10 C atoms. It is therefore particularly vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one CH2 group is replaced by —O—CO— or —CO—O—, this can be linear or branched. Preferably, it is linear and has 2 to 6 C atoms. It is therefore particularly acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionylcxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)-butyl.

Compounds of the formula I having branched end groups R may occasionally be of importance on account of better solubility in the customary liquid crystalline base materials, but in particular as chiral doping substances, if they are optically active. Smectic compounds of this type are suitable as components for ferroelectric materials.

Branched groups of this type as a rule contain not more than one chain branching. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl or 2-methyl-3-oxahexyl.

If R represents an alkyl radical in which two or more CH2 groups are replaced by —O— and/or —CO—O—, this can be linear or branched. Preferably, it is branched and has 3 to 12 C atoms. It is therefore particularly bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarboryl)-methyl, 2,2-bis-(methoxycarbonyl)-ethyl, 3,3-bis-(methoxycarbonyl)-propyl, 4,4-bis-(methoxycarbonyl)-butyl, 5,5-bis(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(methoxycarbonyl)-methyl, 2,2-bis(ethoxycarbonyl)-ethyl, 3,3-bis-(ethoxycarbonyl)-propyl, 4,4-bis-(ethoxycarbonyl)-butyl or 5,5-bis-(ethoxycarbonyl)-pentyl.

Compounds of the formula I which have end groups R suitable for polycondensation available are suitable for the preparation of liquid crystalline polycondensates.

Formula I includes both the racemates of these compounds and the optical antipodes as well as mixtures thereof.

Amongst the compounds of the formulae I and also Ia to Ie, those are preferred in which at least one of the radicals contained therein has one of the meanings indicated as preferred.

A smaller group of preferred compounds of the formula I are those of the sub-formulae I1 to I23:

| | |
|---|---|
| Alkyl-Phe-PF2N | I1 |
| Alkoxy-Phe-PF2N | I2 |
| Alkanoyloxy-Phe-PF2N | I3 |
| Alkoxycarbonyl-Phe-PF2N | I4 |
| Alkyl-Cyc-PF2N | I5 |
| Alkoxy-Cyc-PF2N | I6 |
| Alkanoyloxy-Cyc-PF2N | I7 |
| Alkoxycarbonyl-Cyc-PF2N | I8 |
| Alkyl-Cyc-CH$_2$CH$_2$-PF2N | I9 |
| Alkoxy-Cyc-CH$_2$CH$_2$-PF2N | I10 |
| Alkanoyloxy-Cyc-CH$_2$CH$_2$-PF2N | I11 |
| Alkoxycarbonyl-Cyc-CH$_2$CH$_2$-PF2N | I12 |
| Alkyl-Phe-Phe-PF2N | I13 |
| Alkoxy-Phe-Phe-PF2N | I14 |
| Alkanoyloxy-Phe-Phe-PF2N | I15 |
| Alkoxycarbonyl-Phe-Phe-PF2N | I16 |
| Alkyl-Cyc-Cyc-PF2N | I17 |
| Alkoxy-Cyc-Cyc-PF2N | I18 |
| Alkanoyloxy-Cyc-Cyc-PF2N | I19 |
| Alkoxycarbonyl-Cyc-Cyc-PF2N | I20 |
| Alkyl-Cyc-CH$_2$CH$_2$-Cyc-PF2N | I21 |
| Alkyl-Cyc-CH$_2$O-Phe-PF2N | I22 |
| Alkyl-Cyc-CH$_2$CH$_2$-Phe-PF2N | I23 |

The compounds of the formula I are prepared according to methods which are known per se. as are described in the literature (for example in the standard works such as Houben-Weyl, Methoden der O.ganischen Chemie (Methods of Organic Chemistry), Georg-Thieme-Verlag, Stuttgart), particularly under reaction conditions which are known and suitable for the reactions mentioned. In this way, use can also be made of variants which are known per se and which are not mentioned in more detail here.

If desired, the starting materials may also be formed in situ in such a way that they are not isolated from the reaction mixture but immediately reacted further to give the compounds of the formula I.

Compounds of the formula I are preferably prepared from compounds of the formula II

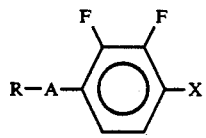

II in which R and A have the meaning indicated and X is H, Cl, CHO or COOH.

Difluorobenzene derivatives of the formula II (X=H) can be deprotonated in a manner known per se using organometallic compounds or base systems (for example, according to A.M. Roe et al., J. Chem. Soc. Chem. Comm. 22, 582 (1965)).

The corresponding lithium compounds may be formulated using formamides, such as dimethylformamide or N-formylpiperidine (X=CHO), carboxylated using carbon dioxide (X=COOH) or reacted directly to give the compounds of the formula I using cyanogen chloride or cyanogen bromide.

The formyl compounds of the formula II are converted in a manner known per se into the nitriles of the formula I (for example J. Streith et al., Helv. Acta 59, 2786 (1976)).

Suitable organometallic compounds are particularly organolithiums, such as, for example, n-, tert- or sec.-butyllithium or methyllithium in an inert solvent, for example an ether such as tetrahydrofursn, dioxane or tert.-butyl methyl ether, a hydrocarbon such as hexane, benzene or toluene or a mixture of these solvents. Preferably, complexing agents, for example amines such as tetramethylethylenediamine (TMEDA) or amides such as hexamethylphosphoric triamide (HMPT) or N,H-dimethylpropyleneurea (DMPH) are added to these solvents Usually, the reaction temperature is between −120° C. and −10° C., preferably between −100° C. and −50° C.

At these temperatures, the deprotonation reactions are complete, as a rule, after 1 to 10 hours.

Furthermore, the compounds of the formula I are preferably prepared by reaction of organotitanium or organozinc with 4-bromo(chloro)-2,3-difluorobenzonitrile under metal catalysis (compare, for example, DE 3,736,489/3,632,410).

The compounds of the formula I may also be prepared by reducing a compound, which otherwise corresponds to the formula I, but contains one or more reducible groups and/or C—C bonds instead of H atoms.

Possible reducible groups are preferably carbonyl groups, in particular keto groups, and in addition, for example, free or esterified hydroxyl groups or aromatically bonded halogen atoms. Preferred starting materials for the reduction correspond to the formula I, but may contain a cyclohexene ring or cyclohexanone ring instead of a cyclohexane ring and/or a —CH=CH— group instead of a —CH$_2$CH$_2$— group and/or a —CO— group instead of a —CH$_2$— group and/or a free or a functionally derived (for example in the form of its p-toluenesulfonate) OH group instead of an H atom.

The reduction may be carried out, for example, by catalytic hydrogenation at temperature: between about 0° and about 200° and pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid or a hydrocarbon such as cyclohexane. Suitable catalysts are preferably noble metals such as Pt or Pd, which can be employed in the form of oxides (for example $PtO_2$, PdO), on a support (for example Pd on carbon, calcium carbonate or strontium carbonate) or in finely divided form.

Ketones may also be reduced by the methods of Clemmensen (using zinc, amalgamated zinc or tin and hydrochloric acid, preferably in aqueous-alcoholic solution or in the heterogeneous phase with water/toluene at temperatures between about 80° and 120°) or Wolff-Kishner (using hydrazine, preferably in the presence of alkali such as KOH or NaOH in a high-boiling solvent such as diethylene glycol or triethylene glycol at temperatures between about 100 and 200°) to give the corresponding compounds of the formula I, which contain alkyl groups and/or —$CH_2CH_2$— bridges.

Furthermore, reductions using complex hydrides are possible. For example, arylsulfonyloxy groups may be removed reductively using $LiAlH_4$, in particular ptoluenesulfonyloxymethyl groups may be reduced to give methyl groups, preferably in an inert solvent such as diethyl ether or THF at temperatures between about 0 and 100°. Double bonds may be hydrogenated (even in the presence of CN groups) using $NaBH_4$ or tributyltin hydride in methanol.

In order to prepare nitriles of the formula I, corresponding acid amides can be dehydrated. The amides are obtainable, for example, from appropriate esters or acid halides by reaction with ammonia. Suitable watereliminating agents are, for example, inorganic acid chlorides such as $SOCl_2$, $PCl_3$, $PCl_5$, $POCl_3$, $SO_2Cl_2$, $COCl_2$, and in addition $P_2O_5$, $P_2S_5$, $AlCl_3$ (for example as the double compound with NaCl), aromatic sulfonic acids and sulfonyl halides. In this way, the reaction can be carried out in the presence or absence of an inert solvent at temperatures between about 0° and 150°; possible solvents are, for example, bases such as pyridine or triethylamine, aromatic hydrocarbons such as benzene, toluene or xylene, or amides such as DMF.

In order to prepare the previously mentioned nitriles of the formula I, appropriate acid halides, preferably the chlorides, can also be reacted with sulfamide, preferably in an inert solvent such as tetramethylene sulfone at temperatures between about 80° and 150°, preferably at 120°. After customary working up, the nitriles can be isolated directly.

The liquid crystalline media according to the invention preferably contain 2 to 40, in particular 4 to 30, components as further constituents in addition to one or more compounds according to the invent on. These media very particularly preferably contain 7 to 25 components in addition to one or more compounds according to the invention. These additional constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl cyclohexane-carboxylates, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid, or of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclocyclohexylbiphenyls, phenyl- or cyclohexylpyrimidines, phenylor cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenyl-cyclohexyl)-ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds can also be fluorinated.

The most important compounds suitable as further constituents of the media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—$CH_2CH_2$—E—R" | 4 |
| R'—L—C≡C—E—R" | 5 |

In the formulae 1, 2, 3, 4 and 5, L and E, which can be identical or different, are in each case independently of one another a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is 1,4-phenylene which is unsubstituted or substituted by fluorine, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)-ethyl, pyrimidine-2,5-diyl, pyridine-2,5-diyl or 1,3-dioxane-2,5-diyl.

Preferably, one of the radicals L and E is Cyc, Phe or Pyr. E is preferably Cyc, Phe or Phe-Cyc. Preferably, the media according to the invention contain one or more components selected from the compounds of the formulae 1, 2, 3, 4 and 5, in which L and E are selected from the group comprising Cyc, Phe and Pyr and, at the same time, one or more components selected from the compounds of the formulae 1, 2, 3, 4 and 5, in which one of the radicals L and E is selected from the group comprising Cyc, Phe and Pyr and the other radical is selected from the group comprising -Phe-Phe-, -Phe-Cyc-, -Cyc-Cyc-, -G-Phe-and -G-Cyc-, and, if desired, one or more components selected from the compounds of the formulae 1, 2, 3, 4 and 5, in which the radicals L and E are selected from the group comprising -Phe-Cyc-, -Cyc-Cyc-, -G-Phe- and -G-Cyc-.

R' and R" in the compounds of the sub-formulae 1a, 2a, 3a, 4a and 5a are in each case independently of one another alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —$CF_3$, F, Cl or —NCS; in this case R has the meaning indicated in the compounds of the sub-formulae 1a to 5a and is preferably alkyl or alkenyl. However, other variants of the substituents proposed in the compounds of the formulae 1, 2, 3, 4 and 5 are also customary. Many of these substances or else mixtures thereof are commercially available. All these substances are obtainable by methods known in the literature or in analogy thereto.

The media according to the invention preferably also contain, in addition to components from the group of compounds 1a, 2a, 3a, 4a and 5a (group 1), components from the group of compounds 1b, 2b, 3b, 4b and 5b (group 2), the proportions of which are preferably as follows: group 1: 20 to 90%, in particular 30 to 90%, group 2: 10 to 80%, in particular 10 to 50%, the sum of the proportions of the compounds according to the invention and the compounds from the groups 1 and 2 being up to 100%.

The media according to the invention preferably contain 1 to 40%, particularly preferably 5 to 30% of compounds according to the invention. Furthermore, media are preferred which contain more than 40%, in particular 45 to 90% of compounds according to the invention. The media preferably contain three, four or five compounds according to the invention.

The preparation of the media according to the invention is carried out in a manner customary per se. As a rule, the components are dissolved in one another, preferably at elevated temperature. By means of suitable additives, the liquid crystalline phases according to the invention can be modified so that they can be used in all types of liquid crystal display elements which have so far been disclosed. Additives of this type are known to the person skilled in the art and are described in detail in the literature (H. Kelker/R. Hatz, Handbook of Liquid Crystals, Verlag Chemie, Weinheim, 1980). For example, pleochroitic dyes may be added to prepare colored guest-host systems or substances may be added to change the dielectric anisotropy, the viscosity and/or the orientation of the nematic phases.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application West German P 38 07 806.6, filed Mar. 10, 1988, are hereby incorporated by reference.

"Customary working up" means: water is added, the mixture is extracted with methylene chloride, the organic phase is separated off, dried and evaporated, and the product is purified by crystallization and/or chromatography.

In addition: C means crystalline/solid state, S means smectic phase (the index distinguishes the phase type), N means nematic state, Ch means cholesteric phase, I means isotropic phase. The number standing between two symbols indicates the conversion temperature in degrees Celsius. m.p.=melting point, c.p.=clear point.

EXAMPLES

Example 1

Preparation of 4-alkyl-4'-cyano-2',3'-difluorobiphenylene (a) 1-(4-Pentylcyclohex-1-enyl)-2,3-difluorobenzene A solution of 0.525 mol of n-butyllithium in 320 ml of hexane is added at $-78°$ C. to a mixture of 0.5 mol of 1,2-difluorobenzene, 1,000 ml of tetrahydrofuran and 0.5 mol of tetramethylethylenediamine. After stirring for 3 hours at $-60°$ C., 0.525 mol of 4-pentylcyclohexanone, dissolved in 100 ml of tetrahydrofuran, is added dropwise and the mixture is allowed to warm slowly to room temperature. The alcohol obtained after neutralization is dissolved without purification in 250 ml of toluene and heated in a water separator with 2 g of ptoluenesulfonic acid for 3 hours. Customary working up gives 1-(4-pentylcyclohex-1-enyl)-2,3-difluorobenzene having a boiling point of 123° C./0.5 torr.

Analogously, 4-(4-propylphenyl)-cyclohexanone as a starting material gives 1-(4-(4-propylphenyl)-cyclohex1-enyl)-2,3-difluorobenzene.

(b) 4-(4-Pentylcyclohex-1-enyl)-2,3-difluorobenzaldehyde 0.12 mol of N-formylpiperidine in 20 ml of tetrahydrofuran is added at -70° C. to 0.1 mol of 4-(4-pentylcyclohex-1-enyl)-2,3-difluorophenyllithium (prepared from the benzene with n-butyllithium in tetrahydrofuran/tetramethylethylenediamine analogously to Example 1a)) and the mixture is warmed to $-20°$ C. during the course of 1 hour. Acidifying and customary working up gives the aldehyde.

(c) 4-(4-Pentylcyclohex-1-enyl)-2,3-difluorobenzonitrile

A mixture of 0.12 mol of hydroxylamine-O-sulfonic acid and 50 ml of water is added at 30° C. to a mixture of 0.1 mol of the aldehyde and 100 ml of water. After stirring for 1 hour at room temperature, the mixture is warmed to 65° C. for 2 hours. Cooling and customary working up gives the nitrile as a white solid. d) Oxidation using 2,3-dichloro-5,6-dicyanobenzoquinone (DDQ)

0.2 mol of DDQ is added to a mixture of 0.1 mol of the cyclohexene derivative from Example 1c) and 200 ml of toluene and the mixture is heated to boiling for 2 hours. Cooling and customary working up give 4-pentyl-4'-cyano-2',3'-difluorobiphenyl.

The following are prepared analogously:
4-ethyl-4'-cyano-2',3'-difluorobiphenyl
4-propyl-4'-cyano-2',3'-difluorobiphenyl
4-butyl-4'-cyano-2',3'-difluorobiphenyl
4-hexyl-4'-cyano-2',3'-difluorobiphenyl
4-heptyl-4'-cyano-2',3'-difluorobiphenyl
4-octyl-4'-cyano-2',3'-difluorobiphenyl
4-ethoxy-4'-cyano-2',3'-difluorobiphenyl
4-propoxy-4'-cyano-2',3'-difluorobiphenyl
4-butoxy-4'-cyano-2',3'-difluorobiphenyl
4-pentoxy-4'-cyano-2',3'-difluorobiphenyl
4-hexoxy-4'-cyano-2',3'-difluorobiphenyl
4-heptoxy-4'-cyano-2',3'-difluorobiphenyl
4-octoxy-4'-cyano-2',3'-difluorobiphenyl
4''-ethyl-4-cyano-2,3-difluoroterphenyl
4''-propyl-4-cyano-2,3-difluoroterphenyl
4''-butyl-4-cyano-2,3-difluoroterphenyl
4''-pentyl-4-cyano-2,3-difluoroterphenyl 4'''-hexyl-4-cyano-2,3-difluoroterphenyl
4'''-heptyl-4-cyano-2,3-difluoroterphenyl
4'''-octyl-4-cyano-2,3-difluoroterphenyl
4'''-ethoxy-4-cyano-2,3-difluoroterphenyl
4'''-propoxy-4-cyano-2,3-difluoroterphenyl
4'''-butoxy-4-cyano-2,3-difluoroterphenyl
4'''-pentoxy-4-cyano-2,3-difluoroterphenyl
4'''-hexoxy-4-cyano-2,3-difluoroterphenyl
4'''-heptoxy-4-cyano-2,3-difluoroterphenyl
4'''-octoxy-4-cyano-2,3-difluoroterphenyl
4-(trans-4-ethylcyclohexylmethoxy)-4'-cyano-2',3'-difluorobiphenyl
4-(trans-4-propylcyclohexylmethoxy)-4'-cyano-2',3'-difluorobiphenyl
4-(trans-4-butylcyclohexylmethoxy)-4'-cyano-2',3'-difluorobiphenyl
4-(trans-4-pentylcyclohexylmethoxy)-4'-cyano-2',3'-difluorobiphenyl
4-(trans-4-hexylcyclohexylmethoxy)-4'-cyano-2',3'-difluorobiphenyl
4-(trans-4-heptylcyclohexylmethoxy)-4'-cyano-2',3'-difluorobiphenyl
4-(trans-4-octylcyclohexylmethoxy)-4'-cyano-2',3'-difluorobiphenyl
1-(4'-cyano-2',3'-difluorobiphenyl-4-yl)-2-(trans-4-ethylcyclohexyl)-ethane
1-(4'-cyano-2',3'-difluorobiphenyl-4-yl)-2-(trans-4-propylcyclohexyl)-ethane
1-(4'-cyano-2',3'-difluorobiphenyl-4-yl)-2-(trans-4-butylcyclohexyl)-ethane
1-(4'-cyano-2',4'-difluorobiphenyl-4-yl)-2-(trans-4-pentylcyclohexyl)-ethane
1-(4'-cyano-2',4'-difluorobiphenyl-4-yl)-2-(trans-4-hexylcyclohexyl)-ethane
1-(4'-cyano-2',4'-difluorobiphenyl-4-yl)-2-(trans-4-heptylcyclohexyl)-ethane
1-(4'-cyano-2',3'-difluorobiphenyl-4-yl)-2-(trans-4-octylcyclohexyl)-ethane

Example 2

Preparation of 4-cyclohexyl-2,3-difluorobenzonitriles

A mixture of 0.1 mol of 4-(4-pentylcyclohex-1-enyl)-2,3-difluorobenzonitrile (prepared according to Example 1a)-1c)), 1.0 g of palladium/active carbon (1%) and 150 ml of toluene is hydrogenated to saturation at room temperature. After filtering and removing the solvent, the residue is dissolved in 150 ml of dimethyl sulfoxide, 12 g of potassium tert.-butoxide are added and the mixture is stirred at room temperature for 2 hours. Acidifying and customary working up gives 4-(trans-4-pentylcyclohexyl)-2,3-difluorobenzonitrile.

The following are prepared analogously:
4-(trans-4-ethylcyclohexyl)-2,3-difluorobenzonitrile
4-(trans-4-propylcyclohexyl)-2,3-difluorobenzonitrile
4-(trans-4-butylcyclohexyl)-2,3-difluorobenzonitrile
4-(trans-4-hexylcyclohexyl)-2,3-difluorobenzonitrile
4-(trans-4-heptylcyclohexyl)-2,3-difluorobenzonitrile
4-(trans-4-octylcyclohexyl)-2,3-difluorobenzonitrile
4-(trans-4-ethoxycyclohexyl)-2,3-difluorobenzonitrile
4-(trans-4-propoxycyclohexyl)-2,3-difluorobenzonitrile
4-(trans-4-butoxycyclohexyl)-2,3-difluorobenzonitrile
4-(trans-4-pentoxycyclohexyl)-2,3-difluorobenzonitrile
4-(trans-4-hexoxycyclohexyl)-2,3-difluorobenzonitrile
4-(trans-4-heptoxycyclohexyl)-2,3-difluorobenzonitrile
4-(trans-trans-4-ethylbicyclohexyl-4'-yl)-2,3-difluorobenzonitrile
4-(trans-trans-4-propylbicyclohexyl-4'-yl)-2,3-difluorobenzonitrile
4-(trans-trans-4-butylbicyclohexyl-4'-yl)-2,3-difluorobenzonitrile
4-(trans-trans-4-pentylbicyclohexyl-4'-yl)-2,3difluorobenzonitrile
4-(trans-trans-4-hexylbicyclohexyl-4'-yl)-2,3-difluorobenzonitrile
4-(trans-trans-4-heptylbicyclohexyl-4'-yl)-2,3-difluorobenzonitrile
4-(trans-trans-4-octylbicyclohexyl-4'-yl)-2,3-difluorobenzonitrile
4-[trans-4-(trans-4-ethylcyclohexylethyl)cyclohexyl]-2,3-difluorobenzonitrile
4-[trans-4-(trans-4-propylcyclohexylethyl)cyclohexyl]-2,3-difluorobenzonitrile
4-[trans-4-(trans-4-butylcyclohexylethyl)cyclohexyl]-2,3-difluorobenzonitrile
4-[trans-4-(trans-4-pentylcyclohexylethyl)cyclohexyl]-2,3-difluorobenzonitrile
4-[trans-4-(trans-4-hexylcyclohexylethyl)cyclohexyl]-2,3-difluorobenzonitrile
4-[trans-4-(trans-4-heptylcyclohexylethyl)cyclohexyl]-2,3-difluorobenzonitrile
4-[trans-4-(trans-4-octylcyclohexylethyl)cyclohexyl]-2,3-difluorobenzonitrile

Example 3

Preparation of 4-(2-(trans-4-alkylcyclohexyl)-ethyl)2,3-difluorobenzonitriles (a)

1-(2,3-Difluorophenyl)-2-trans-4-pentylcyclohexyl)ethane

A solution of 0.21 mol of n-butyllithium in 130 ml of hexane is added at −100° C. to a mixture of 0.25 mol of 1,2-difluorobenzene, 0.20 mol of potassium tert.-butoxide and 200 ml of tetrahydrofuran. After stirring for 10 minutes, a mixture of 0.2 mol of 2-(trans-4-pentylcyclohexyl)-ethyl iodide, 0.2 mol of dimethylaminopropyleneurea and 50 ml of tetrahydrofuran is added at −90° C. to the mixture. Stirring for 1 hour at −40° C. and customary working up gives the ethane derivative having a boiling point of 135° C./0.5 torr and, in addition, a little 1,4-di-(2-trans-4-pentylcyclo-hexyl)ethyl)-2,3-difluorobenzene as a by-product having C 64° C. N 106 7° I.

(b)

4-(2-(Trans-4-pentylcyclohexyl)-ethyl)-2,3-difluorobenzonitrile.

0.1 mol of the ethane derivative is deprotonated according to Example 1a), formulated according to Example 1b) and reacted with 0.12 mol of hydroxylamine-O-sulfonic acid according to Example 1c). Customary working up gives the nitrile as a colorless solid, C 38° N (16.3°) I.

The following are prepared analogously:
4-(2-(trans-4-ethylcyclohexyl)-ethyl)-2,3-difluorobenzonitrile
4-(2-(trans-4-propylcyclohexyl)-ethyl)-2,3-difluorobenzonitrile
4-(2-(trans-4-butylcyclohexyl)-ethyl)-2,3-difluorobenzonitrile
4-(2-(trans-4-hexylcyclohexyl)-ethyl)-2,3-difluorobenzonitrile 4-(2-(trans-4-heptylcyclohexyl)-ethyl)-2,5-difluorobenzonitrile 4-(2-(trans-4-octylcyclohexyl)-ethyl)-2,3-difluorobenzonitrile 4-(2-(trans-4-ethoxycyclohexyl)-ethyl)-2,3-difluorobenzonitrile 4-(2-(trans-4-propoxycyclohexyl)-ethyl))-2,3-difluorobenzonitrile 4-(2-(trans-4-butoxycyclohexyl)-ethyl)-2,3-difluorobenzonitrile 4-(2-(trans-4-pentoxycyclohexyl)-ethyl)-2,3-difluorobenzonitrile 4-(2-(trans-4-hexoxycyclohexyl)-ethyl)-2,3-difluorobenzonitrile 4-(2-(trans-4-heptoxycyclohexyl)-ethyl)-2,3-difluorobenzonitrile 4-(2-(trans-4-octoxycyclohexyl)-ethyl)-2,3-difluorobenzonitrile Example 4

Preparation of 4-alkyl-2,3'-difluoro-4'-cyanobiphenylene.

0.1 mol of chlorotriisopropyl orthotitanate in 20 ml of tetrahydrofuran is added at 5° C. to a mixture of 1-bromomagnesium-4-propylbenzene (prepared from 0.1 mol of 4-propyl-bromobenzene and 0.1 mol of magnesium) and 90 ml of tetrahydrofuran and the mixture is stirred at 5° to 20° C. for 30 minutes. A mixture of 1.3 g of bis-(triphenylphosphine)-nickel(II) chloride and 0.1 mol of 4-bromo-2,3-difluorobenzonitrile (prepared from 1-trimethylsilyl-2,3-difluorobenzene by conversion into the nitrile analogously to Example 1a) 1c) and subsequent bromination with bromine with removal by distillation of the resulting trimethylsilyl bromide) is added to this mixture. Stirring for 24 hours at room temperature and customary working up gives 4-propyl-2',3'-difluoro-4'-cyanobiphenyl.

The following are prepared analogously:
4-ethyl-2',3'-difluoro-4'-cyanobiphenyl
4-butyl-2',3'-difluoro-4'-cyanobiphenyl
4-pentyl-2',3'-difluoro-4'-cyanobiphenyl
4-hexyl-2',3'-difluoro-4'-cyanobiphenyl
4-heptyl-2',3'-difluoro-4'-cyanobiphenyl
4-octyl-2',3'-difluoro-4'-cyanobiphenyl Example A A nematic liquid crystal mixture is prepared which is composed of
15% of 2,3-difluoro-4-(trans-4-propylcyclohexylethyl)-benzonitrile,
15% of 2,3-difluoro-4-(trans-4-butylcyclchexylethyl)-benzonitrile,
10% of 2,3-difluoro-4-(trans-4-pentylcyclohexylethyl)-benzonitrile,
9% of trans-4-propylcyclohexyl trans-4-propylcyclohexanecarboxylate,
9% of trans-4-pentylcyclohexyl trans-4-propylcyclohexanecarboxylate,
6% of p-propylphenyl trans-4-(trans-4-propylcyclohexyl)cyclohexane-carboxylate,
6% of p-pentylphenyl trans-4-(trans-4-propylcyclohexyl)cyclohexane-carboxylate,
6% of p-pentylphenyl trans-4-(trans-4-butylcyclohexyl)cyclohexane-carboxylate,
6% of p-propylphenyl trans-4-(trans-4-butylcyclohexyl)cyclohexane-carboxylate,
6% of p-trans-4-propylcyclohexylphenyl trans-4-butylcyclohexane-carboxylate,
6% of p-trans-4-propylcyclohexylphenyl trans-4-pentylcyclohexane-carboxylate,
3% of 4,4'-bis-(trans-4-propylcyclohexyl)-2-fluorobiphenyl and
3% of 4-(trans-4-pentylcyclohexyl)-4'-(trans-4-propylcyclohexyl)-2-fluorobiphenyl.

Example B

A nematic liquid crystal mixture is prepared which is composed of
15% of p-trans-4-propylcyclohexyl-benzonitrile,
8% of 4-ethyl-2',3'-difluoro-4'-cyanobiphenyl,
7% of 4-propyl-2',3'-difluoro-4'-cyanobiphenyl,
8% of 4-butyl-2',3'-difluoro-4'-cyanobiphenyl,
5% of p-methoxyphenyl trans-4-propylcyclohexanecarboxylate,
4% of p-ethoxyphenyl trans-4-propylcyclohexanecarboxylate,
5% of p-methoxyphenyl trans-4-butylcyclohexanecarboxylate,
4% of p-ethoxyphenyl trans-4-butylcyclohexanecarboxylate,
4% of p-ethoxyphenyl trans-4-pentylcyclohexanecarboxylate,
4% of p-methoxyphenyl trans-4-pentylcyclohexanecarboxylate,
6% of p-propylphenyl trans-4-(trans-4-propylcyclohexyl)-cyclohexanecarboxylate,
6% of p-pentylphenyl trans-4-(trans-4-propylcyclohexyl)cyclohexanecarboxylate,
5% of p-pentylphenyl trans-4-(trans-4-butylcyclohexyl)-cyclohexanecarboxylate,
5% of p-propylphenyl trans-4-(trans-4-butylcyclohexyl)-cyclohexanecarboxylate,
8% of p-propylphenylp-trans-4-propylcyclohexylbenzoate and
6% of p-propylphenylp-trans-4-pentylcyclohexylbenzoate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystalline phase containing at least two liquid crystalline components, the improvement wherein at least one component is a 2,3-difluorobenzonitrile of the formula

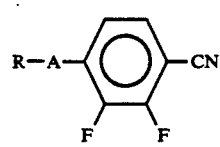

wherein
R is alkyl of 1-12 C atoms or alkyl of 1-12 C atoms in which one or two CH₂ groups ar replaced by —O—, —CO—, —O—CO—, and/or —CH=—, where two O atoms are not directly linked with one another, and
A is

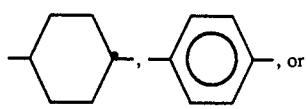

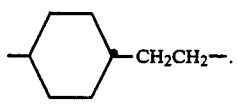

2. A liquid crystalline phase of claim 1, wherein R is alkyl or alkoxy.
3. A liquid crystalline phase of claim 2, wherein R is straight chained.
4. A liquid crystalline phase of claim 3, wherein R is 3-7 C atoms.
5. A liquid crystalline phase of claim 1, wherein R is alkyl wherein one $CH_2$ group is replaced by —O—CO—.
6. A liquid crystalline phase of claim 1, wherein A is

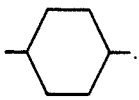

7. In a liquid crystal display element containing a liquid crystalline phase, the improvement wherein said phase is one of claim 1.
8. In an electrooptical display element containing a liquid crystalline dielectric, this improvement wherein said dielectric is a liquid crystalline phase of claim 1.
9. A liquid crystalline phase according to claim 1, wherein A is

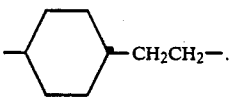

10. A liquid crystalline phase according to claim 1, wherein A is

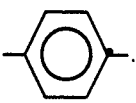

11. A liquid crystalline phase according to claim 1, wherein A is

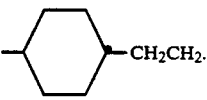

12. In a liquid crystalline phase containing at least two liquid crystalline components, the improvement wherein at least one component is a 2,3-difluorobenzonitrile of the formula

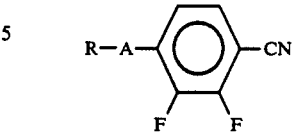

wherein
R is alkyl of 1-12 C atoms or alkyl of 1-12 C atoms in which one or two $CH_2$ groups are replaced by —O—, —CO—, —O—CO—, and/or —CH=CH—, wherein two O atoms are not directly linked with one another, and
A is

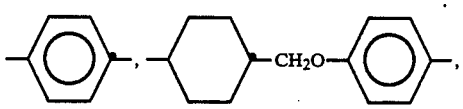

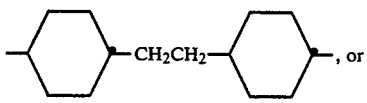

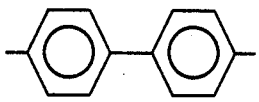

13. A liquid crystalline phase according to claim 12, wherein A is

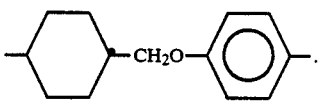

14. A liquid crystalline phase according to claim 12, wherein A is

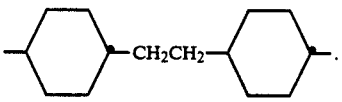

15. A liquid crystalline phase according to claim 12, wherein A is

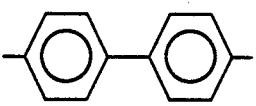

16. A liquid crystalline phase according to claim 12, wherein R is alkyl or alkoxy.
17. A liquid crystalline phase according to claim 12, wherein R is straight chained.
18. A liquid crystalline phase according to claim 12, wherein R is 3-7 C atoms.
19. A liquid crystalline phase according to claim 12, wherein R one $CH_2$ group is replaced by —O—CO—.
20. In a liquid crystal display element containing a liquid crystalline phase, the improvement wherein said phase is one of claim 12.
21. In an electrooptical display element containing a liquid crystalline dielectric, this improvement wherein said dielectric is a liquid crystalline phase of claim 12.

* * * * *